(12) United States Patent
Bertrand et al.

(10) Patent No.: US 9,744,122 B2
(45) Date of Patent: *Aug. 29, 2017

(54) TOPICAL FORMULATION FOR PAIN RELIEF

(71) Applicants: Helene Bertrand, North Vancouver (CA); Marylene Kyriazis, West Vancouver (CA)

(72) Inventors: Helene Bertrand, North Vancouver (CA); Marylene Kyriazis, West Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/141,872

(22) Filed: Apr. 29, 2016

(65) Prior Publication Data

US 2016/0243025 A1  Aug. 25, 2016

Related U.S. Application Data

(63) Continuation-in-part of application No. 14/260,367, filed on Apr. 24, 2014, now Pat. No. 9,351,985.

(60) Provisional application No. 61/816,913, filed on Apr. 29, 2013.

(51) Int. Cl.
| | |
|---|---|
| *A61K 31/065* | (2006.01) |
| *A61K 31/045* | (2006.01) |
| *A61K 9/00* | (2006.01) |
| *A61K 31/047* | (2006.01) |
| *A61K 31/7004* | (2006.01) |
| *A61K 47/10* | (2017.01) |
| *A61K 47/14* | (2017.01) |
| *A61K 47/24* | (2006.01) |
| *A61K 47/34* | (2017.01) |

(52) U.S. Cl.
CPC .......... *A61K 9/0014* (2013.01); *A61K 31/047* (2013.01); *A61K 31/7004* (2013.01); *A61K 31/045* (2013.01); *A61K 47/10* (2013.01); *A61K 47/14* (2013.01); *A61K 47/24* (2013.01); *A61K 47/34* (2013.01)

(58) Field of Classification Search
CPC ............................. A61K 31/045; A61K 31/047

USPC ......................................... 514/726, 724, 738
See application file for complete search history.

(56) References Cited

U.S. PATENT DOCUMENTS

| | | | |
|---|---|---|---|
| 4,600,711 A | 7/1986 | Swerczek | |
| 4,808,610 A * | 2/1989 | Munayyer | A61K 31/58 514/419 |
| 5,420,114 A | 5/1995 | Clodman | |
| 5,720,962 A * | 2/1998 | Ivy | A61K 45/06 424/401 |
| 9,351,985 B2 * | 5/2016 | Bertrand | A61K 9/0014 |
| 2009/0131537 A1 | 5/2009 | Wille, Jr. | |
| 2012/0121721 A1 | 5/2012 | James | |
| 2012/0230968 A1 | 9/2012 | Worden, Sr. | |
| 2013/0236577 A1 | 9/2013 | Rosen | |

FOREIGN PATENT DOCUMENTS

| | | |
|---|---|---|
| CN | 1038644 C | 6/1998 |
| WO | 2008073324 A1 | 6/2008 |

OTHER PUBLICATIONS

Rabogo et al., "Hypertonic Dextrose Injections (Prolotherapy) for Knee Osteoarthritis: Results of a Single-Arm Uncontrolled Study with 1-Year Follow-up", The Journal of Alternative and Complementary Medicine, vol. 18, No. 4, 2012, pp. 408-414.
Waili, Topical Honey Application vs. Acyclovir for the Treatment of Recurrent Herpes Simplex Lesions, Medi Sci Monit, 2004; 10(8): MT94-98.
Brown et al., "Dermal and Transdermal Drug Delivery Systems: Current and Future Prospects", Drug Delivery, 13:175-187, 2006.
Levon et al., "Ultrasound and Transdermal Drug Delivery", DDT vol. 9, No. 15 Aug. 2004.
L. Cavone, et al. ,Topical Mannitol Reduces Inflammatory Edema in a Rat Model of Arthritis, Jan. 10, 2012.

* cited by examiner

*Primary Examiner* — Kevin E Weddington
(74) *Attorney, Agent, or Firm* — Larson & Larson, P.A.; Frank Liebenow

(57) ABSTRACT

Described herein are topical pain compositions comprising between 15 and 90% mannitol, for use in the treatment of pain, itch and other cutaneous nerve conditions. The resulting compositions may be in the form of creams, gels, lotions, ointments, foams, suppositories, and sprays.

18 Claims, No Drawings

TOPICAL FORMULATION FOR PAIN RELIEF

CROSS-REFERENCE TO RELATED APPLICATION

This application is a non-provisional application taking priority from U.S. patent application Ser. No. 14/260,367, filed Apr. 24, 2014, which in turn takes priority from U.S. patent application Ser. No. 61/816,913, filed Apr. 29, 2013, the disclosure of which are hereby incorporated by reference.

FIELD

This invention relates to the field of topical formulations for pain relief, and more particularly to mannitol-based topical formulations for conditions in which cutaneous nerves may be involved.

BACKGROUND

Oral pain relievers are typically prescribed for treatment of acute and chronic pain, including arthritic pain, musculoskeletal pain, and neuropathic pain. Oral pain relievers often have side effects, some of which can be severe. Topical pain relievers work locally and are less likely to cause severe systemic side effects. Some topical pain relievers include non-steroidal anti-inflammatory drugs (NSAIDs), salicylates, lidocaine, capsaicin, amitriptyline, glyceryl trinitrate, opioids, menthol, and gabapentin.

Research suggests that NSAIDs are most effective as topical pain relievers for a number of conditions including joint-related conditions; however, they may not be suitable for all subjects experiencing pain, due to allergies, drug intolerances or contraindications such as renal failure, hypertension or gastric ulcers from absorption of topical NSAIDs.

Some other topical pain relievers are classified as counterirritants, such as menthol, capsaicin and camphor, which work by creating a burning or cooling sensation that distracts the person from the actual pain. Capsaicin in particular causes undesirable side effects including burning and stinging.

There is a need for alternative topical pain relievers with minimal side effects, and without unpleasant localized cooling and burning sensations.

Mannitol is a sugar alcohol with the formula $C_6H_8(OH)_6$. It reduces intracellular water retention and also has free radical scavenging properties. Mannitol's most common uses are related to its function as an osmotic diuretic, thereby making it a suitable agent for treating kidney failure, reducing swelling in the brain and eye, and treating cystic fibrosis. Mannitol is also used as a sweetener in chewing gum and for diabetics.

Mannitol has been shown to be effective in pain management when injected under the skin or intravenously. For example, intravenous mannitol reduces neuro-inflammation by reducing edema. In addition, injection of mannitol just under the skin is used to treat neuropathic pain. Finally, dental anaesthesia is more effective when mannitol is included with the standard nerve block agents, lidocaine and epinephrine.

Mannitol has been used for treating pain intravenously and subcutaneously, but never topically.

SUMMARY

In one embodiment, the invention is a topical pain relief composition comprising mannitol and at least one excipient.

In another embodiment, the present is a topical pain relief composition comprising between 15 and 90% mannitol by weight in a mixture comprising propylene glycol, purified water, isopropyl palmitate, caprylic/capric triglyceride, ceteareth 20, cetearyl alcohol, glyceryl stearate, PEG-100 stearate, dimethicone, octyldodecanol, lecithin, ethylhexylglycerin, and phenoxyethanol.

In another embodiment, the present is a topical pain relief composition comprising between 15 and 90% mannitol by weight, between 0.25% and 20% of menthol by weight, in a mixture comprising propylene glycol, purified water, isopropyl palmitate, caprylic/capric triglyceride, ceteareth 20, cetearyl alcohol, glyceryl stearate, PEG-100 stearate, dimethicone, octyldodecanol, lecithin, ethylhexylglycerin, and phenoxyethanol.

In yet another embodiment, the present is a use of a topical composition comprising between 15 and 90% mannitol by weight for topically treating pain, itch and other conditions involving cutaneous nerves.

DETAILED DESCRIPTION

A new route of administration for mannitol for the specific indication of pain is disclosed. The topical composition allows for transdermal delivery of mannitol. This specific composition produces a cosmetically elegant product that enables mannitol to be readily absorbed through the skin providing relief of pain within seconds to minutes. In some testing, pain relief has shown to last anywhere from two hours to up to 48 hours. No adverse effects from the use of the cream have been reported. The ingredients, including mannitol, are typically classified as natural health products.

Mannitol is mixed with one or more suitable excipients to maximize transdermal delivery. In some embodiments, mannitol is incorporated into a cream, gel, lotion, ointment, foam, suppository, or a spray, using methods known in the art. Suitable excipients include emulsifiers, organogelators and emollients. Emulsifiers include polyethylene glycol stearate, a glycol stearate, a glyceryl stearate, cetearyl alcohol and ceteareth 20, methylcellulose, Cetomacrogol 1000, and lecithin. Suitable organogelators include 4-tertbutyl-1-aryl cyclohecanols derivatives, polymeric (e.g. poly(ethylene glycol), polycarbonate, polyesters, and poly(alkylene), Gemini gelators (e.g. N-lauroyl-L-lysine ethyl ester), Boc-Ala(1)-Aib(2)-β-Ala(3)-OMe (synthetic tripeptide), and low molecular weight gelators (e.g. fatty acids and n-alkanes). Suitable emollients include cetostearyl alcohol, cetyl alcohol, isopropyl palmitate, caprylic/capric triglyceride, PPG-2 myristyl ether propionate, dimethicone, methicone, petrolatum, lanolin, and mineral oil.

If desired, other additives including surfactants, penetration enhancers, preservatives, viscosity modifiers, and emulsion stabilizers may be included in the mannitol compositions. Suitable surfactants include sodium lauryl sulfate, cetostearyl alcohol, ceteareth 12, ceteareth 20, cetearyl alcohol, Cetomacrogol 1000, stearic acid, and poloxamer. Suitable penetration enhancers include propylene glycol. Suitable preservatives include methylparaben, propylparaben, ethylhexylglycerin, phenoxyethanol, chlorocresol, potassium sorbate, sorbic acid, bronopol, methychloroisothiazolinone, and methylisothiazolinone. Suitable viscosity modifiers include carboxymethylcellulose, carboxyethylcellulose, acrylate crosspolymer, and carbomer. Suitable emulsion stabilizers include xanthan gum, glyceryl stearate, and carbomer. If desired, other additives may be included to modify the colour or aroma of the topical compositions described herein.

In one embodiment, mannitol is incorporated to a final weight percentage between 15 and 90% in a mixture comprising propylene glycol, purified water, isopropyl palmitate, caprylic/capric triglyceride, ceteareth 20, cetearyl alcohol, glyceryl stearate, PEG-100 stearate, dimethicone, octyldodecanol, lecithin, ethylhexylglycerin, and phenoxyethanol.

In other embodiments, mannitol is incorporated into other suitable carriers known in the art.

Mannitol is much more effectively absorbed through skin when menthol is included in the composition, leading to improved pain relief. Therefore, an improved topical composition includes from 0.25% up to 20.0% of menthol, by weight. Although any amount of menthol within this range is anticipated, 1.25% by weight has been shown to be effective.

Mannitol and menthol is mixed with one or more suitable excipients that maximize transdermal delivery. In some embodiments, mannitol is incorporated into a cream, gel, lotion, ointment, foam, suppository, or a spray, using methods known in the art. Suitable excipients include emulsifiers, organogelators and emollients. Emulsifiers include polyethylene glycol stearate, a glycol stearate, a glyceryl stearate, cetearyl alcohol and ceteareth 20, methylcellulose, Cetomacrogol 1000, and lecithin. Suitable organogelators include 4-tertbutyl-1-aryl cyclohecanols derivatives, polymeric (e.g. poly(ethylene glycol), polycarbonate, polyesters, and poly(alkylene), Gemini gelators (e.g. N-lauroyl-L-lysine ethyl ester), Boc-Ala(1)-Aib(2)-β-Ala(3)-OMe (synthetic tripeptide), and low molecular weight gelators (e.g. fatty acids and n-alkanes). Suitable emollients include cetostearyl alcohol, cetyl alcohol, isopropyl palmitate, caprylic/capric triglyceride, PPG-2 myristyl ether propionate, dimethicone, methicone, petrolatum, lanolin, and mineral oil.

If desired, other additives including surfactants, penetration enhancers, preservatives, viscosity modifiers, and emulsion stabilizers may be included in the mannitol compositions. Suitable surfactants include sodium lauryl sulfate, cetostearyl alcohol, ceteareth 12, ceteareth 20, cetearyl alcohol, Cetomacrogol 1000, stearic acid, and poloxamer. Suitable penetration enhancers include propylene glycol. Suitable preservatives include methylparaben, propylparaben, ethylhexylglycerin, phenoxyethanol, chlorocresol, potassium sorbate, sorbic acid, bronopol, methychloroisothiazolinone, and methylisothiazolinone. Suitable viscosity modifiers include carboxymethylcellulose, carboxyethylcellulose, acrylate crosspolymer, and carbomer. Suitable emulsion stabilizers include xanthan gum, glyceryl stearate, and carbomer. If desired, other additives may be included to modify the colour or aroma of the topical compositions described herein.

In one embodiment, mannitol is incorporated to a final weight percentage between 15 and 90%, along with menthol to a final weight percentage between 0.25% and 20.0%, in a mixture comprising propylene glycol, purified water, isopropyl palmitate, caprylic/capric triglyceride, ceteareth 20, cetearyl alcohol, glyceryl stearate, PEG-100 stearate, dimethicone, octyldodecanol, lecithin, ethylhexylglycerin, and phenoxyethanol.

In other embodiments, mannitol is incorporated into other suitable carriers known in the art.

The resulting mannitol-based topical composition can be used to treat many conditions in which cutaneous nerves are involved, including acute pain, chronic pain, autoimmune disorders, itching, eczema, psoriasis, pain and itching associated with mosquito bites, wasp and bee stings, spider bites and burns; neuropathic pain such as diabetic neuropathy, postherpetic neuralgia, osteoarthritis, headaches, neck and back pain and tendonitis.

Inventors' own studies suggest the effectiveness of mannitol as a topical pain reliever is distinct from its osmotic effects, and is at least partly due to down-regulation of the TRPV1 receptor. The TRPV1 receptor is present on sensory nerves in the skin and is implicated in neurogenic inflammation, acute pain and chronic pain.

Mannitol has not been used for treating pain through the topical route of administration. Furthermore, mannitol has not been used via any route (neither subcutaneous nor topical) for the treatment of other conditions associated with cutaneous nerves (aside from pain), such as itching and autoimmune disorders.

Equivalent elements can be substituted for the ones set forth above such that they perform in substantially the same manner in substantially the same way for achieving substantially the same result.

What is claimed is:

1. A method of treating cutaneous nerve pain, the method comprising:
   preparing a topical composition comprising between 15% and 90% mannitol by weight, and at least one excipient, the excipient comprising at least one emulsifier; wherein the emulsifier is at least one of the group consisting of a polyethylene glycol stearate, a glycol stearate, a glyceryl stearate, cetearyl alcohol and ceteareth 20, methylcellulose, Cetamacrogol 1000, and lecithin; and
   applying the topical composition onto skin;
   wherein the at least one excipient is at least one of an organogelator and an emollient.

2. The method of claim 1 wherein the topical composition is one of a cream, gel, lotion, ointment, foam, suppository, and spray.

3. The method of claim 1 wherein the topical composition further comprises at least one additive selected from the group consisting of surfactants, penetration enhancers, preservatives, viscosity modifiers, and emulsion stabilizers.

4. The method of claim 1 wherein the the emollient is at least one of cetostearyl alcohol, cetyl alcohol, isopropyl palmitate, caprylic/capric triglyceride, PPG-2 myristyl ether propionate, dimethicone, methicone, petrolatum, lanolin, and mineral oil.

5. The method of claim 1 wherein the organogelator is at least one of 4-tertbutyl-1-aryl cyclohecanols derivatives, a polymeric, polycarbonate, polyesters, and poly(alkylene), Gemini gelators, Boc-Ala(1)-Aib(2)-β-Ala(3)-OMe (synthetic tripeptide), low molecular weight gelators, fatty acids and n-alkanes.

6. The method of claim 3 wherein the surfactant comprises at least one of sodium lauryl sulfate, cetostearyl alcohol, ceteareth 12, ceteareth 20, cetearyl alcohol, Cetomacrogol 1000, stearic acid, and poloxamers.

7. The method of claim 3, wherein the penetration enhancer comprises at least one of menthol from 0.25% to 20.0% by weight.

8. The method of claim 3, wherein the preservative comprises at least one of methylparaben, propylparaben, ethylhexylglycerin, phenoxyethanol, chlorocresol, potassium sorbate, sorbic acid, bronopol, methychloroisothiazolinone, and nnethylisothiazolinone.

9. The method of claim 3, wherein the viscosity modifiers are at least one of carboxymethylcellulose, carboxyethylcellulose, acrylate crosspolymer, and carbomer.

10. The method of claim 3, wherein the emulsion stabilizers are at least one of xanthan gum, glyceryl stearate, and carbomer.

11. A method of treating cutaneous nerve pain, the method comprising:

preparing a topical composition comprising between 15% and 90% mannitol by weight, and at least one excipient; the at least one excipient comprising an emollient; wherein the emollient is at least one of cetostearyl alcohol, cetyl alcohol, isopropyl palmitate, caprylic/capric triglyceride, PPG2 myristyl ether propionate, dimethicone, methicone, petrolatum, lanolin, and mineral oil; and applying the topical composition onto skin;

wherein the at least one excipient further comprises at least one of an emulsifier, and an organogelator.

12. The method of claim 11, wherein the topical composition further comprises at least one additive selected from the group consisting of surfactants, penetration enhancers, preservatives, viscosity modifiers, and emulsion stabilizers.

13. The method of claim 11, wherein the emulsifier is at least one of a polyethylene glycol stearate, a glycol stearate, a glyceryl stearate, cetearyl alcohol and ceteareth 20, methylcellulose, Cetomacrogol 1000, and lecithin.

14. A method of treating cutaneous nerve pain, the method comprising:

preparing a topical pain relief composition comprising between 15 and 90% mannitol by weight; between 0.25% and 20.0% menthol by weight; and at least one excipient, the at least one excipient comprising an organogelator; the organogelator is at least one of 4-tertbutyl-1-aryl cyclohecanols derivatives, polymeric, polycarbonate, polyesters, and poly(alkylene), Gemini gelators, Boc-Ala(1)Aib(2)-β-Ala(3)-OMe (synthetic tripeptide), and low molecular weight gelators.

15. The method of claim 14, wherein the at least one excipient further comprises at least one of an emulsifier and an emollient.

16. The method of claim 14 wherein the topical composition further comprises at least one additive selected from the group consisting of surfactants, penetration enhancers, preservatives, viscosity modifiers, and emulsion stabilizers.

17. The method of claim 15, wherein the emulsifier is at least one of a polyethylene glycol stea rate, a glycol stearate, a glyceryl stearate, cetearyl alcohol and ceteareth 20, methylcellulose, Cetomacrogol 1000, and lecithin.

18. The method of claim 15, wherein the emollient is at least one of cetostearyl alcohol, cetyl alcohol, isopropyl palmitate, caprylic/capric triglyceride, PPG-2 myristyl ether propionate, dimethicone, methicone, petrolatum, lanolin, and mineral oil.

* * * * *